US00PP27862P3

(12) United States Plant Patent
Randag

(10) Patent No.: US PP27,862 P3
(45) Date of Patent: Apr. 4, 2017

(54) CALLA LILY PLANT NAMED 'UNIVERSE'

(50) Latin Name: *Zantedeschia sprengeri*
Varietal Denomination: Universe

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 82 days.

(21) Appl. No.: 14/544,439

(22) Filed: Jan. 7, 2015

(65) Prior Publication Data

US 2015/0296690 P1 Oct. 15, 2015

Related U.S. Application Data

(60) Provisional application No. 61/964,771, filed on Apr. 11, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV—International Union for the Protection of New Varieties of Plants: PLUTO Plant Variety Database; May 19, 2016; cultivar name—'Universe' (1 pg).*

* cited by examiner

*Primary Examiner* — Susan McCormick Ewoldt
(74) *Attorney, Agent, or Firm* — The Webb Law Firm

(57) ABSTRACT

'Universe' is a new variety of calla lily having inflorescences with a dark yellow-colored spathe that produces 4-15 inflorescences per tuber. The inflorescence stems are about 30 cm in height, and the leaves are green with whitish spots and have a leathery texture.

3 Drawing Sheets

Botanical classification: *Zantedeschia sprengeri*.
Varietal denomination: 'UNIVERSE'.

BACKGROUND OF THE NEW PLANT

The present invention comprises a new and distinct cultivar of calla lily, botanically known as *Zantedeschia sprengeri* and hereinafter referred to by the cultivar name 'Universe'.

'Universe' is a product of a planned breeding program which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* seedling Z010450 (female parent, unpatented) with a *Zantedeschia sprengeri* selection referred to as C02003 (male parent, unpatented). 'Universe' was selected in 2006 by the inventor in 't Zand, The Netherlands as one flowering plant within the progeny of the stated cross.

The first act of asexual reproduction of 'Universe' by tissue culture was performed by the inventor in September of 2007 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Universe' which, in combination, distinguish this calla lily as a new and distinct cultivar:

1. Dark yellow-colored spathe;
2. Compact growth habit; and
3. High inflorescence production.

Further, when compared to calla lily plant named 'Yellow Jacket BLZ' (U.S. Plant Pat. No. 20,217), 'Yellow Jacket BLZ' has an upper surface spathe color of Yellow Group RHS 7A and a lower surface spathe color of Yellow Group RHS 7B, while the upper surface spathe color of 'Universe' varies between Yellow Group RHS 9A and 9B and the lower surface spathe color varies between Green Group RHS 143A and 143B. When compared to calla lily plant named 'Sunclub' (pending U.S. Plant patent application Ser. No. 14/544,261), 'Sunclub' exhibits a lanceolate leaf shape, while 'Universe' has a sagittate leaf shape. Further, the upper surface spathe color of 'Sunclub' varies between Yellow Group RHS 12A and 12B, while the upper surface spathe color of 'Universe' varies between Yellow Group RHS 9A and 9B.

Table 1 provides similarities and differences of 'Universe' to its parents, *Zantedeschia sprengeri* seedling Z010450 and selection C02003.

TABLE 1

| 'Universe' | Similarities | Differences |
|---|---|---|
| Z010450 | Spathe shape | Spathe color (Between Yellow Group RHS 9D to 10C)<br>Plant height (10-40 cm) |
| C02003 | Spathe color | Number of inflorescences (5-15)<br>Plant height (5-30 cm)<br>Leaf shape (Lanceolate) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

THE PLANT

Figure 1:
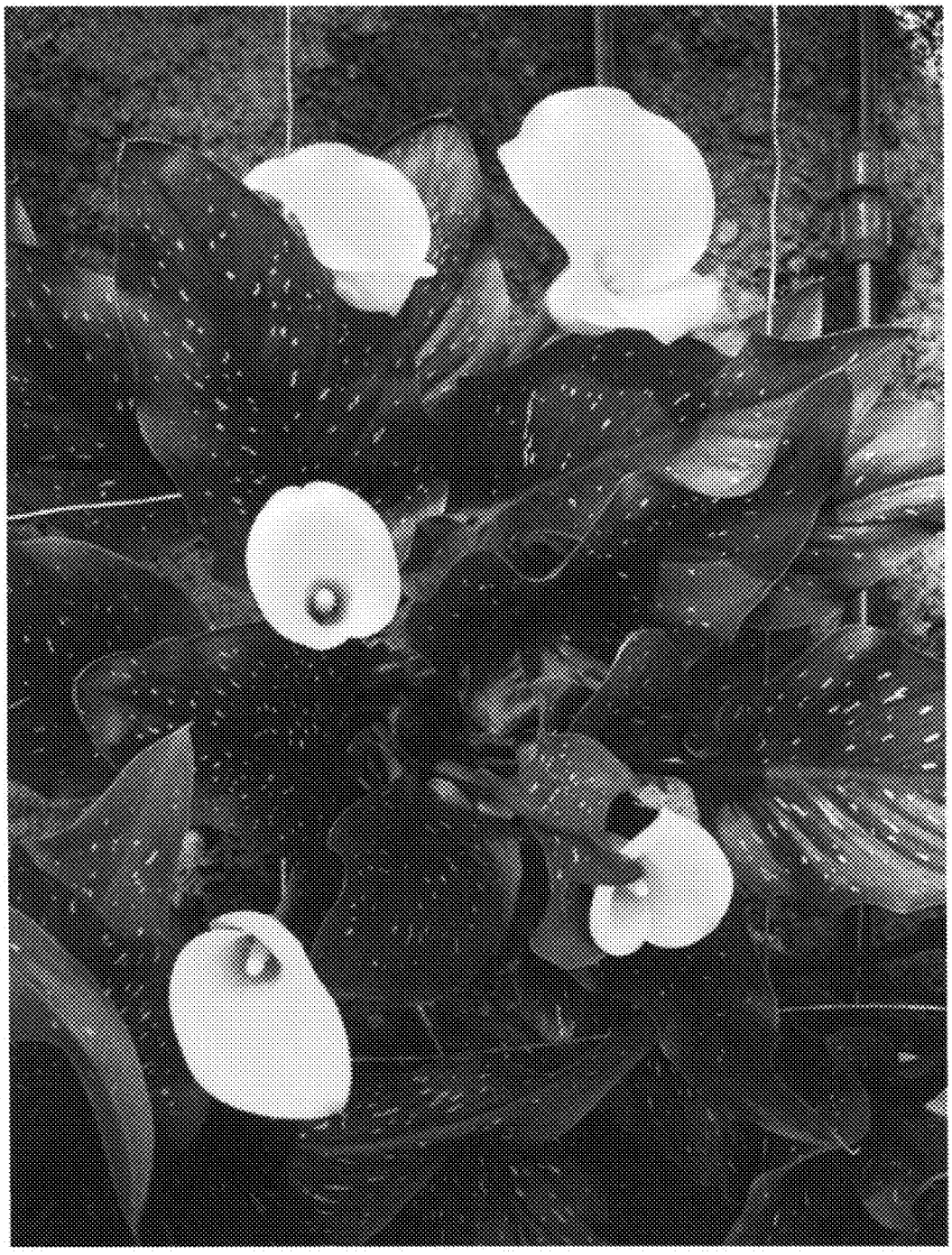
FIG. 1 is a photograph of an overhead view of a single plant of the new variety.
Figure 2:
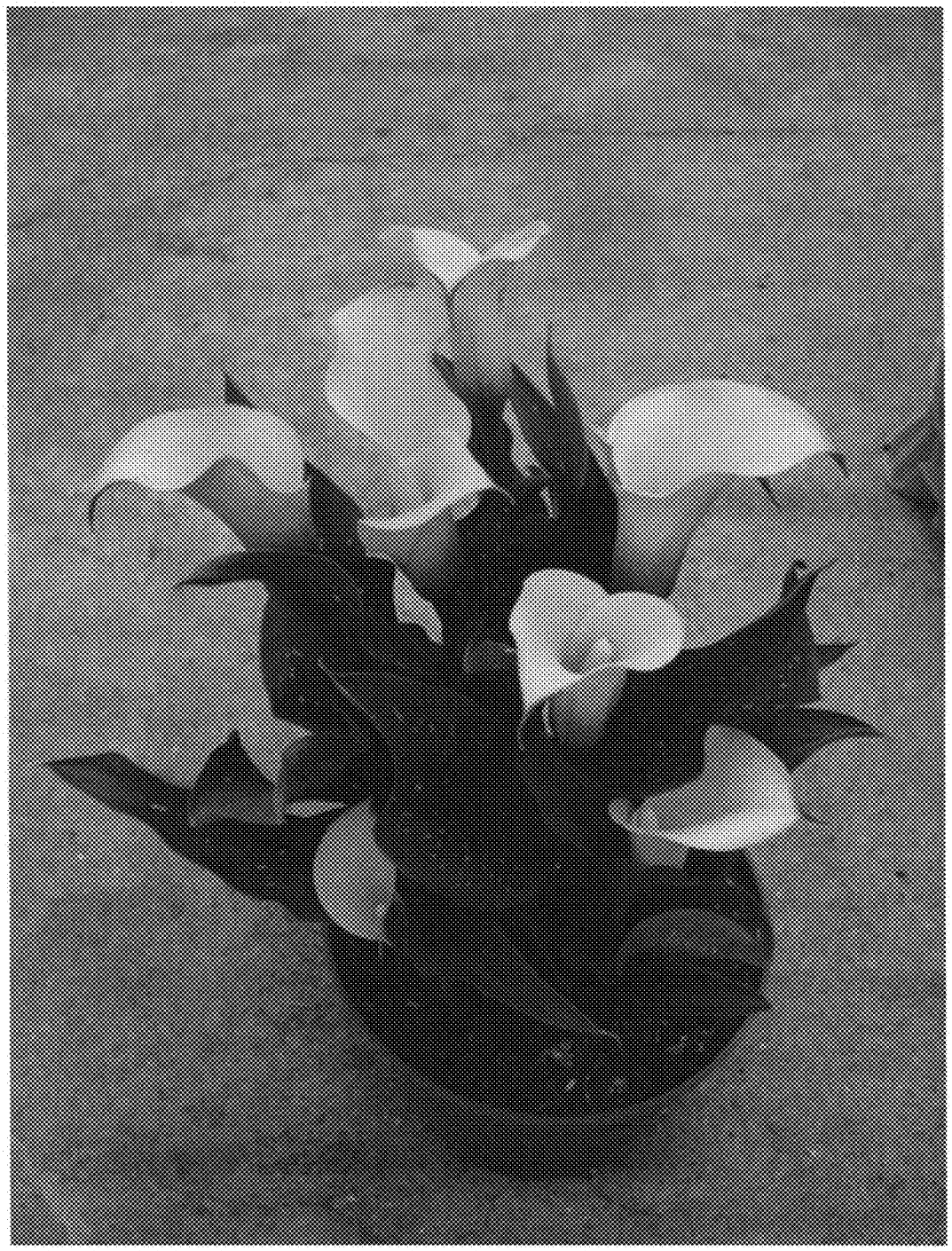
FIG. 2 is a photograph of a single plant of the new variety grown in a pot.
Figure 3:
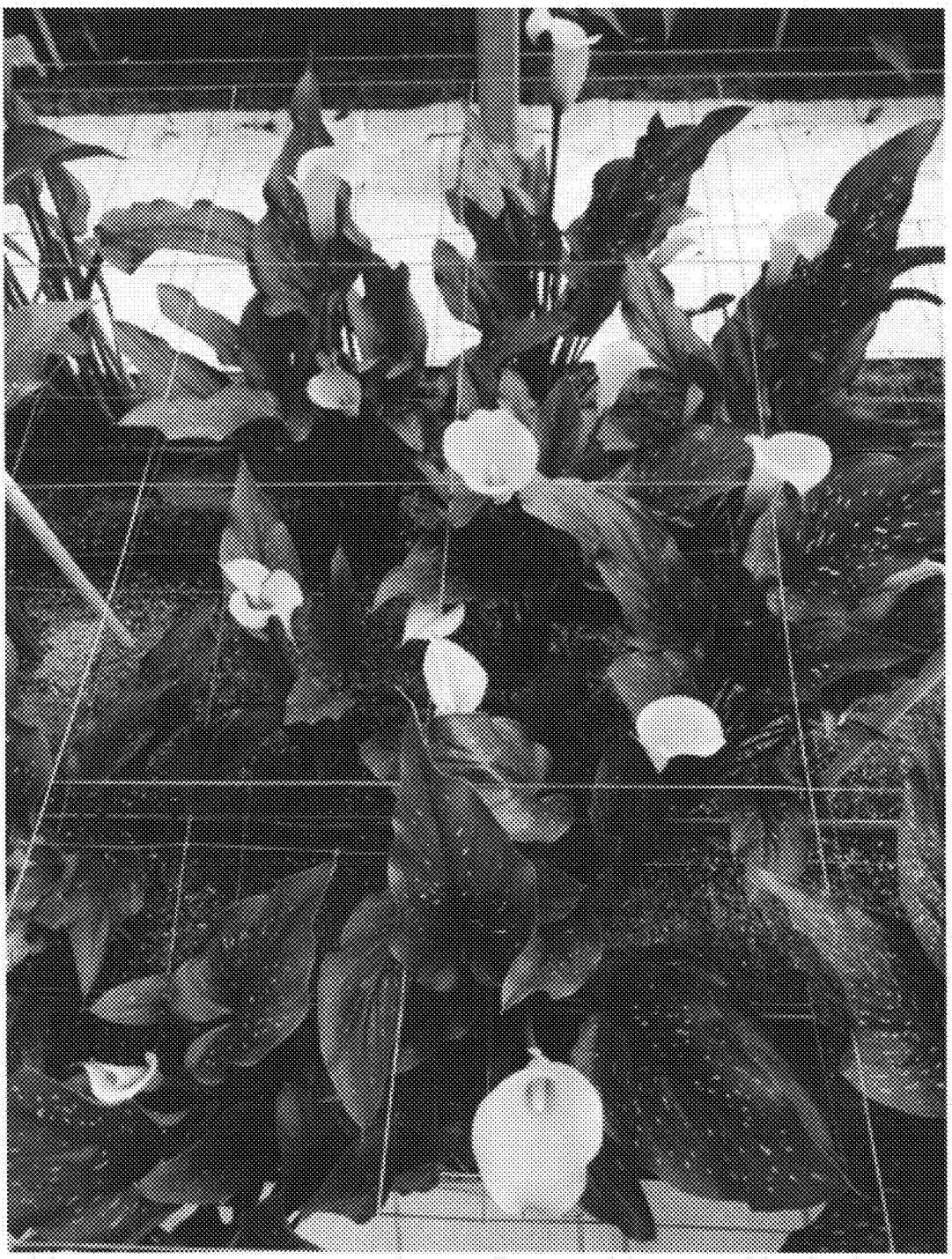
FIG. 3 is a photograph of a group of multiple plants of the new variety.

Size:

*Height of the leaf canopy above the soil.*—4-32 cm.

*Height of top of inflorescence above the soil.*—7-30 cm.

*Diameter.*—15-40 cm.

Form: Erect.

Number of inflorescences per tuber:

*Size* 14-16 cm *in diameter.*—4-9 inflorescences.

*Size* 16-18 cm *in diameter.*—5-10 inflorescences.

*Size* 18-20 cm *in diameter.*—6-15 inflorescences.

Branches:

*Character.*—Many (from 3-8); like the variety 'Odessa' (U.S. Plant Pat. No. 18,833).

*Color.*—Between Greyed-Purple Group RHS N186C and N187A.

Leaves:

*Size.*—Width: 2.5-12 cm. Length: 6-20 cm.

*Number per plant.*—20-35.

*Shape.*—Sagittate.

*Color.*—Upper surface: Green Group RHS 139A to 139B, with transparent White Group RHS 155A and N155A spots. Lower surface: Green Group RHS N138B to N138C, with transparent White Group RHS 155A and N155A spots.

*Apex.*—Acute.

*Base.*—Sagittate.

*Margin.*—Undulate; having a color of Green Group RHS 139A to 139B.

*Veins.*—Configuration: Pinnate. Color: Green Group RHS 143A to 143B.

*Surface quality.*—Leathery.

*Petiole.*—Length: 4-20 cm. Diameter: 7 mm. Color: The base is White Group RHS 155A, and the upper part is Yellow-Green Group RHS 144A to 144B.

Roots:

*Color.*—White.

*Branching.*—Similar to other *Zantedeschia* varieties.

THE INFLORESCENCE AND SEEDS

Spathe:

*Size.*—Length (measured from base opening to tip): 3-6 cm. Width: 3-5 cm. Height: 3-7 cm.

*Color.*—Upper surface: Varies between Yellow Group RHS 9A and 9B. Lower surface: Varies between Green Group RHS 143A and 143B.

*Vein color.*—Between Yellow Group RHS 9A and 9B.

*Shape.*—Cupped.

*Apex.*—Obtuse.

*Base.*—Rounded.

*Texture.*—Smooth (upper and lower surfaces).

Spadix:

*Size.*—Length: 30-45 mm. Diameter: 3-10 mm.

*Color.*—Between Yellow Group RHS 6A and 6C.

*Position relative to spathe.*—Upright.

Peduncle:

*Size.*—Length: 5-22 cm. Diameter: 3-8 mm.

*Color.*—The upper part is between Green Group RHS 143A and 143B, and the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Yellow Group RHS 6A and 6C.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Green-Yellow Group RHS 1A and 1B.

*Ovaries.*—Texture: Smooth. Length: Between 1 to 10 mm. Width: Between 1 to 10 mm. Color: Top color is between Yellow-Green Group RHS 145A and 145B, bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-50.

Fruit:

*Amount.*—Multiple berries produced.

*Shape.*—Irregular.

*Color*.—Varies between Yellow-Green Group RHS N144B to 145D.

GENERAL

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Universe' as herein described and illustrated.

* * * * *